(12) United States Patent
Kunimune

(10) Patent No.: US 8,137,704 B2
(45) Date of Patent: Mar. 20, 2012

(54) METHOD OF MANUFACTURING DIGESTIBLE POWDER THAT GENERATES HYDRIDE ION (H-)

(76) Inventor: Tetsunori Kunimune, Burbank, CA (US)

(*) Notice: Subject to any disclaimer, the term of this patent is extended or adjusted under 35 U.S.C. 154(b) by 259 days.

(21) Appl. No.: 12/716,564

(22) Filed: Mar. 3, 2010

(65) Prior Publication Data

US 2011/0217390 A1 Sep. 8, 2011

(51) Int. Cl.
*A01N 59/06* (2006.01)
*A61K 33/06* (2006.01)

(52) U.S. Cl. ............... 424/682; 423/637; 423/647

(58) Field of Classification Search ............... None
See application file for complete search history.

(56) References Cited

U.S. PATENT DOCUMENTS 2,082,134 A * 6/1937 Alexander ............... 423/647
2,401,326 A * 6/1946 Archibald et al. ............ 423/647

FOREIGN PATENT DOCUMENTS

JP 2005245265 A * 9/2005

\* cited by examiner

*Primary Examiner* — Johann Richter
*Assistant Examiner* — Daniel L Branson
(74) *Attorney, Agent, or Firm* — Scott Lam, Esq.

(57) ABSTRACT

A method of manufacturing digestible powder that generates a hydride ion (H−) when dissolved in water is provided. A vacuum oven system that can reach 600° C. and $10^{-5}$ torr is used within this method. The method according to this current application comprises of ten to eleven steps of vacuuming, heating and hydrogen treatment of coral reef powder. By adding mixtures of magnesium, phosphorus and potassium, the maximum treating temperature and vacuum pressure is lowered. The coral reef powders treated via the ten steps emit hydrogen when dissolved in the water like powders that are treated with a mixture of natural form of magnesium, phosphorus and potassium complex. Those natural form of the magnesium, phosphorous and potassium includes $(NH_4)MgPO_4 \cdot 6H_2O$ (struvite), $MgSO_4 \cdot KCl \cdot H_2O$ (Kainite), $K_2SO_4 \cdot MgSO_4 \cdot 6H_2O$ (Schönite), $K_2SO_4 \cdot MgSO_4 \cdot 4H_2O$ (Leonite), and $K_2SO_4 \cdot 2MgSO_4$ (Langbeinite).

12 Claims, 6 Drawing Sheets

大人の血球の顕微鏡写真図

Translation: Photomicrograph of the adult blood cell.

Translation: Photomicrograph of the adult blood cell after eating or drinking

METHOD OF MANUFACTURING DIGESTIBLE POWDER THAT GENERATES HYDRIDE ION (H-)

FIELD OF THE INVENTION

The current invention relates to a method of manufacturing digestible powder that generates the hydride ion from natural coral reef with lower temperatures.

BACKGROUND OF THE INVENTION

The hydride ion (H⁻), was until recently considered to be primarily the province of plasma physicists. This form of hydrogen, where the atom bears an extra electron (e⁻) was thought to be extremely short-lived on the surface of the earth at standard pressures and temperatures (STP), and rather, it was considered to primarily exist, at least for any lifetime beyond a few nano-seconds, in plasmas in the laboratory and in the interior of stars. Recently, the hydride ion has been found to be quite plentiful in the earth's interior and even on the surface of the earth. Perhaps even more surprisingly, although there have only been small hints of this phenomenon in the biochemistry literature since the 1930s or earlier, the hydride ion plays a critical role in all known life forms on earth. The hydride ion acts as both an energy carrier and as an antioxidant in numerous biological systems. In its antioxidant role, this ion functions as a powerful primal, primitive, primeval, primordial and primary antioxidant found in all raw, unprocessed foods and in many "wild" unprocessed, untreated water sources in the biosphere.

Some methods of providing chemical components that produce the hydride ion (H⁻) in the human body have been published. However, those methods are not clear and may be dangerous in terms of causing cancer.

It is the purpose of this current application to provide a more economical method to produce the hydride ion (H⁻) in a form of a non-carcinogenic material.

DESCRIPTION OF THE PRIOR ART

U.S. Pat. Nos. 7,632,969 and 7,208,626 to Welz-Biermann, et al. disclosed a process for the preparation of perfluoroalkylphosphines comprising at least the reaction of at least one fluoro (perfluoroalkyl)phosphorane with at least one hydride ion donor, and to the use of tris(perfluoroalkyl) phosphines as perfluoroalkylating reagents.

U.S. Pat. No. 7,582,759 to Niddam-Hildesheim, et al. illustrates a diastereomerically pure rosuvastatin and processes for preparing diastereomerically pure rosuvastatin and its intermediates, wherein the reaction mixture contains about 1.5 to about 4 equivalents of hydride ion per gram of rosuvastatin keto-ester.

U.S. Pat. Nos. 7,407,905 and 6,887,813 to Ginosar, et al. illustrated a method of re-activating a catalyst, comprising: providing a catalyst at least partially deactivated by at least one fouling agent; contacting the catalyst with a fluid reactivating agent at or above a critical point thereof, the fluid reactivating agent comprising a source of a hydride ion; transferring the hydride ion from the fluid reactivating agent to the at least one fouling agent; and releasing the at least one fouling agent from the catalyst.

U.S. Pat. No. 6,911,564 Khachik illustrates a process for converting (3R,3'R,6'R)-lutein to a mixture of anhydroluteins I, II, III, (3R,6'R)-α-cryptoxanthin and (3R)-β-crypto xanthin, comprising reacting (3R,3'R,6'R)-lutein in the presence of a strong acid and a hydride ion donor of triethylsilane in a chlorinated solvent or toluene under an inert atmosphere to give a mixture of anhydroluteins I, II, III, (3R,6'R)-α-cryptoxanthin and (3R)-β-cryptoxanthin.

U.S. Pat. No. 5,766,482 to Bertan disclosed a process for capture, degradation, and destruction of a sulfur bearing compound, comprising: contacting said sulfur bearing compound with a mixture of a metal insoluble with said sulfur bearing compound, a reducing agent of a hydride ion, and a base; and capturing, degrading, and destroying said sulfur bearing compound in said mixture of said metal insoluble with said sulfur bearing compound, said reducing agent, U.S. Pat. Nos. 5,653,968 and 5,653,969 Carballada, et al. illustrates a rinse-off hair care compositions that contains hydride ion.

U.S. Pat. Nos. 5,225,339 and 5,342,767 to Wong, et al. disclosed a process for transferring a hydride ion from an R-alcohol to the pro-R position of NADP.

U.S. Pat. Nos. 5,220,020, 5,227,538, 5,286,878 and 5292893 to Buchwald, et al. illustrates a catalytic asymmetric reduction process, wherein a silane compound able to supply a hydride ion during the reduction reaction.

U.S. Pat. No. 4,338,289 to Shore, et al. disclosed a method for the preparation of decaborane-14($B_{10}H_{-14}$) through the conversion of $B_5H_9$ to $[N(CH_3)_4][B_9H_{14}]$, the hydride ion abstraction reaction of $[N(CH_3)_4][B_9H_{14}]$, by a boron trihalide to form $B_{10}H_{14}$, and the separation and recovery of $B_{10}H_{14}$, in pure form by a sublimation process. U.S. Pat. No. 4,089,853 to Lanzilotti A process for the preparation of cis-5,6-Dimethoxy-2-methyl-3-[2-(4-phenyl-1-piperazinypethyl]indoline which comprises ionically hydrogenating 5,6-dimethoxy-2-methyl-3-[2-(4-phenyl-1-piperazinyl)ethyl]indole with a hydrogenation pair consisting essentially of a proton donor selected from the group consisting of concentrated phosphoric acid, concentrated sulfuric acid, trifluoroacetic acid and polyphosphoric acid and a hydride ion donor selected from the group consisting of di(alkyl $C_1$-$C_3$)silanes, tri(alkyl $C_1$-$C_3$)silanes, diphenylsilane and triphenylsilane at a temperature of from about 25 to about 65° C. for a period of time sufficient for a substantial degree of $\Delta^2$-hydrogenation to occur.

U.S. Pat. No. 4,072,605 to Thelander illustrates a method and process for removal by precipitation of salts of a variety of metallic elements from aqueous solutions such as an alkali hydroxide is added to activate the reaction through controlling the reduction of free iodine and activates the free electrons of the phosphorous atom of said phosphorous acid in the conjugated base form by means of the proposed intermediate hydride ion which in turn, releases these electrons for reduction purposes.

U.S. Pat. Nos. 3,931,242 and 3,980,730 to Dawans, et al. illustrates a catalysts in the stereospecific polymerisation of unsaturated organic compounds, which has a formula of $(H_{3-n}X_n)C-CO_2M(CO)_m(R)_p(L)_q$ in which X is fluorine, bromine or chlorine with the provision that at least one X is fluorine, n is an integer selected from 1, 2 and 3, M is a metal selected from the group consisting of molybdenum and tungsten, R is selected from the group consisting of a hydride ion, or a methyl, ethyl, allyl, methallyl, crotyl, phenyl or benzyl group, L is a Lewis base selected from the group consisting of aliphatic monoethers, aliphatic diethers, aliphatic monoether-monoalcohols, and aliphatic mono- and diketones, m is an integer from 1 to 3 inclusive, p is 1 and q is an integer selected from the values 1 to 2, with the proviso that the values of m, p and q are such that, in the valence shell of said metal M, the sum of the number of electrons contributed by said metal M and the number of electrons contributed by the ligands is 18.

None of the Prior art disclose a method of providing a hydride ion (H⁻) generating material except the following:

In the 1990's Patrick Flanagan claimed discovery of negatively charged hydrogen or hydride ions in the Hunza water. Crystal Energy® contains Microcluster® silica (the active ingredient in Silica Hydride) is the only known supplement to dramatically increase zeta potential. It is claimed that these ions act as powerful antioxidants. A nutritional supplement was developed using silica micro clusters to stabilize the hydride ions, a novel compound known as Silica Hydride. Blood cell test was done with a mixture of 500 mg of Silica Hydride, a blend of Microcluster® silica (aggregates of 50 angstrom diameter micro sphere) and active hydrogen mixed with 8 oz of water as shown in FIGS. 3 and 4.

Japanese Patent JP 4404657 to Taneaki Oikawa insists that coral calcium can be used as a resource of eatable hydrogen an-ion generating materials by treating the material with two steps of oxidization and reduction. Coral Reefs are large underwater structures of coral skeletons, made from calcium carbonate ($CaCO_3$) secreted by generation after generation of tiny coral polyps over sometimes millions of years of coral growth in the same location One method is to mix coral calcium powder 55 wt % and flour 45 wt % with water and make pastes. The pastes were molded and dried. It is oxidized with firing for 4 hours with 700° C. After oxidized, it is reduced in the $N^2$ and $H^2$ gas climate at the reduction furnace for 4 hours at 650° C. The final material generates hydrogen an-ion (H⁻) when eaten by a user.

Another method of producing eatable hydrogen an-ion is;

Mix 40 g of coral calcium or calcium carbonate, 30 g of silica, flour 30 grams are mixed as the raw materials and pasted with water, then it is dried. It is oxidized with firing for 4 hours with 700° C. After oxidized, it is reduced in the $N^2$ and $H^2$ gas climate at the reduction furnace for 4 hours at 650° C.

The inventor claimed that the product changes the blood cell cluster structure after a user ate their product, reference in FIG. 5 and FIG. 6.

When Calcium Carbonate ($CaCO_3$) is exposed to high temperature above 825° C., carbon dioxide ($CO_2$) is generated leaving CaO behind. This process is reversible, since once the CaO is cooled, it immediately begins to absorb carbon dioxide from the air, until, after enough time, and it is completely converted back to calcium carbonate.

However, the temperature to decompose the calcium carbonate ($CaCO_3$) is still too high. Several attempts were done to find out to lower the decomposition temperature. Yoshida et al., (1999, Catalyst letter Vol/58, ppp 119'121) discloses a method of preparing calcium oxide (CaO) from calcium carbonate at a lower temperature with the aid of catalysts of Palladium (Pd) and Irridium(Ir) and Hydrogen under vacuum as follows.

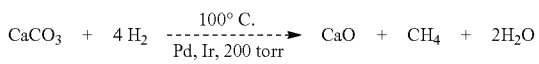

In 2006, BERUTO et al., published a method of decomposing calcium carbonate at a lower temperature under vacuum in the *Journal of American Chemical Society*, Vol 3, 439~443, as shown below.

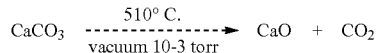

As a conclusion, the Japanese Patent JP 4404657 (2009 Nov. 13) take concept of Mr. Flanaga's concept and change the core material from silica to calcium oxide because crystalline silica is know as carcinogenic compound.

But, whatever the real hydrogen form the temperature disclosed in the Japanese Patent is still high and nothing is clear what their final form is. The role of the flour is not clearly explained and the residual hydrocarbon also is concerned as carcinogenic.

SUMMARY OF THE INVENTION

The hydride ion (H⁻), was until recently considered to be primarily the province of plasma physicists. This form of hydrogen, where the atom bears an extra electron (e) was thought to be extremely short-lived on the surface of the earth at standard pressures and temperatures (STP), and rather, it was considered to primarily exist, at least for any lifetime beyond a few nano-seconds, in plasmas in the laboratory and in the interior of stars. Recently, the hydride ion has been found to be quite plentiful in the earth's interior and even on the surface of the earth. Perhaps even more surprisingly, although there have been hints of this phenomenon in the literature of biochemistry since the 1930s or earlier, the hydride ion plays a critical role in all known life forms on earth. It acts as both an energy carrier and as an antioxidant in numerous biological systems. In its antioxidant role, this ion functions as a powerful primal, primitive, primeval, primordial and primary antioxidant found in all raw, unprocessed foods and in many "wild" unprocessed, untreated water sources in the biosphere. Some methods of providing the chemical components that produce the hydride ion (H⁻) in human body are published. However, most of the methods are not clear and dangerous in terms of causing cancer. It is the purpose of current application to provide a more economical method to produce the hydride ion (H⁻) in a form of non-carcinogenic material. A method of manufacturing digestible powder that generates hydride ion (H⁻) when dissolved in water is provided. A vacuum oven system that can reach 600° C. and $10^{-5}$ torr is used. The method according to current application comprises of ten to eleven steps of vacuuming, heating and hydrogen treatment. By adding mixtures of magnesium, phosphorus and potassium, the maximum treating temperature and vacuum pressure is lowered. The coral reef powders treated via the ten steps emit hydrogen when dissolved in the water like the powders that are treated a mixture of natural form of magnesium, phosphorus and potassium complex. Those natural form of the magnesium, phosphorous and potassium includes $(NH_4)MgPO_4 \cdot 6H_2O$ (struvite), $MgSO_4 \cdot KCl \cdot H_2O$ (Kainite), $K_2SO_4 \cdot MgSO_4 \cdot 6H_2O$ (Schönite), $K_2SO_4 \cdot MgSO_4 \cdot 4H_2O$ (Leonite), and $K_2SO_4 \cdot 2MgSO_4$ (Langbeinite).

DETAILED DESCRIPTION OF THE PREFERRED EMBODIMENT

Figure 1:
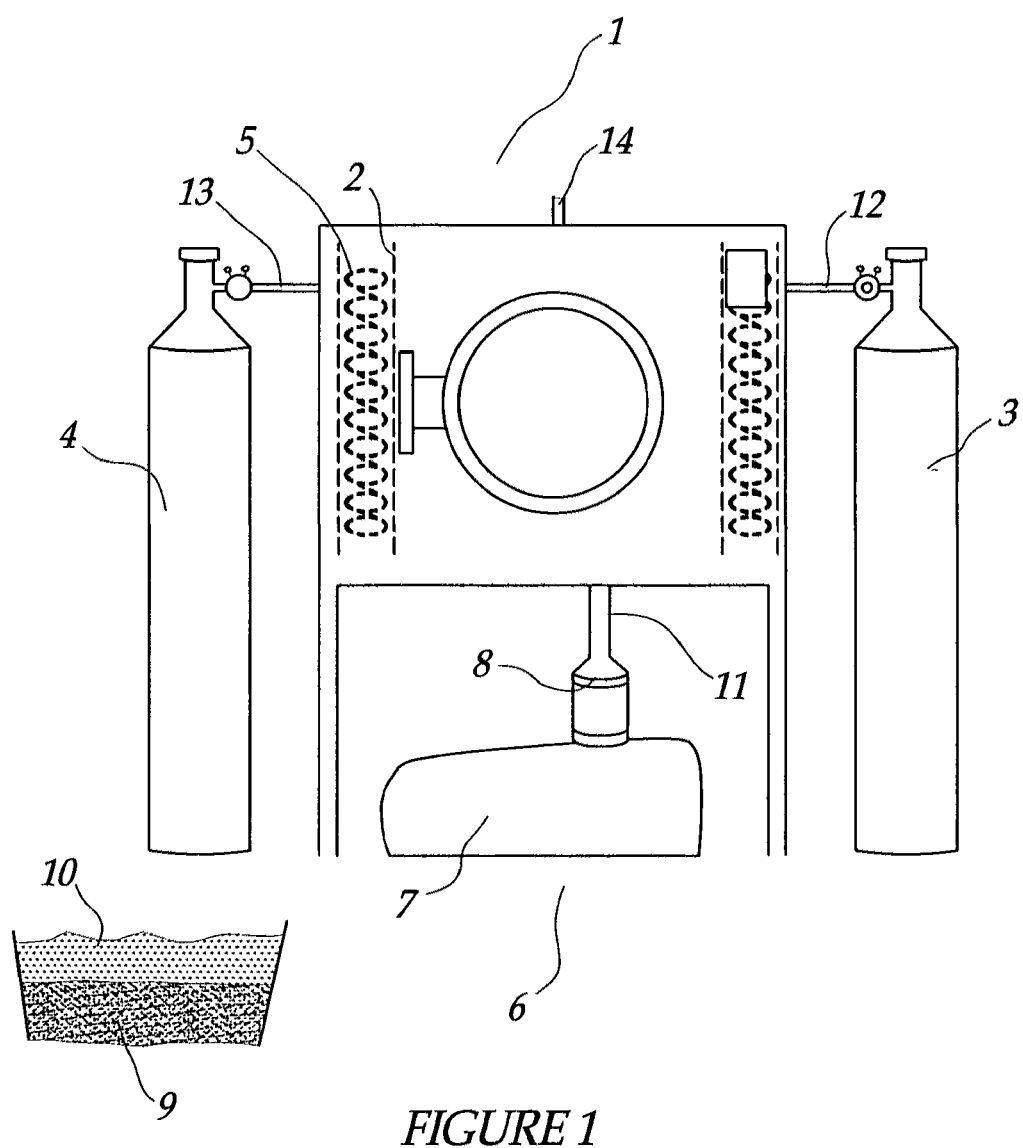
FIG. 1 is a schematic drawing of the process used in preparing a digestible powder that generates hydride ion (H⁻) according to current application

FIG. 1 is a schematic drawing of the process (1) used in preparing a digestible powder that generates hydride ion (H⁻) according to current application. The process (1) comprises of one vacuum oven (2) and hydrogen gas cylinder (3) and nitrogen gas cylinder (4). The vacuum oven (2) is equipped with heater (5) (shown as dotted line inside) that can raise and control the oven temperature up to 1,000° C. and a vacuum pump (6) that is comprised of a mechanical vacuum pump (7) that can vacuum the oven (2) down to $10^{-2}$ and a diffusion pump (8) that can vacuum the oven (2) down to $10^{-5}$.

Figure 2:
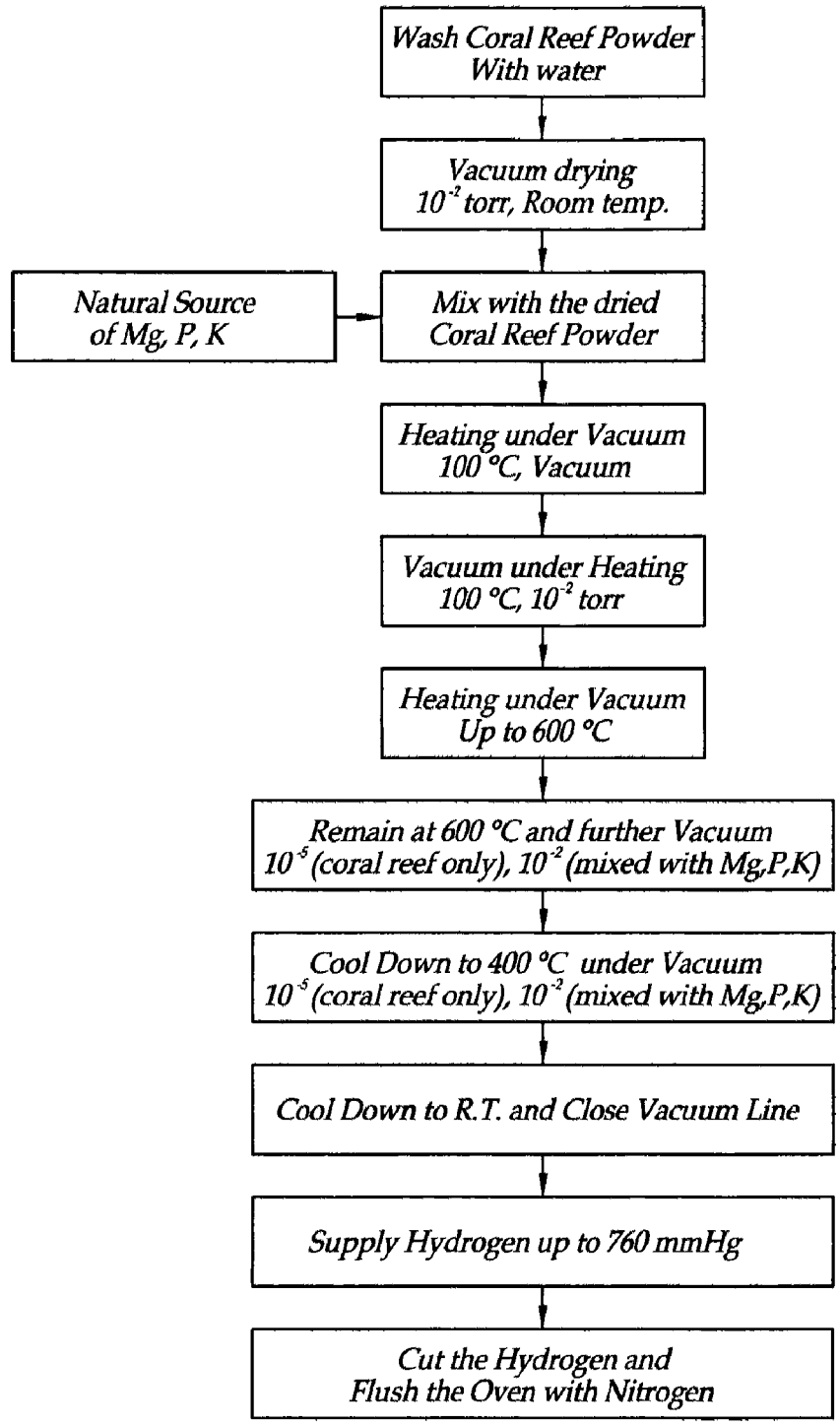
FIG. 2 is a schematic drawing of the procedure to make the digestible powder that generates hydride ion (H⁻) according to current application.
Figure 3:
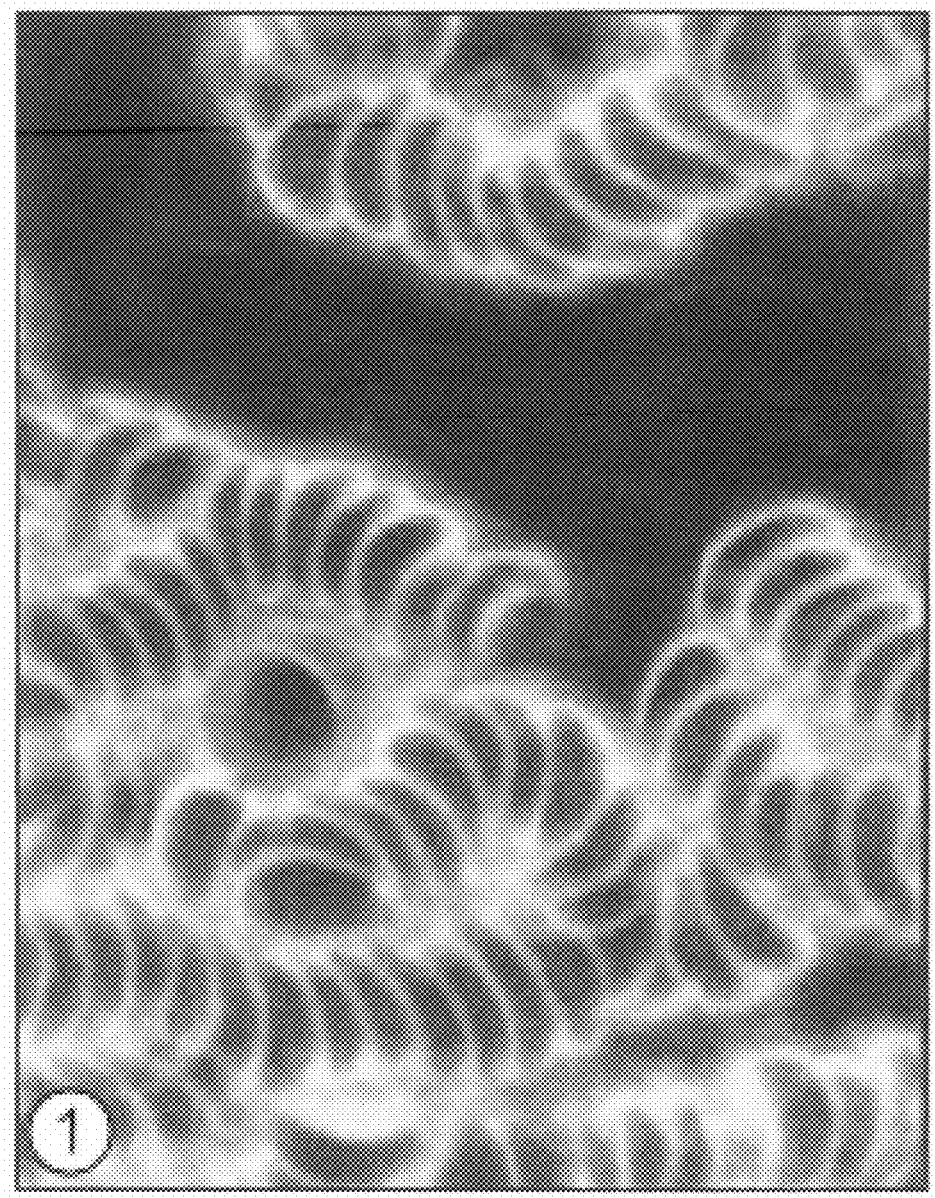
FIG. 3 shows blood cells which are clustered together and trap waste elements between them, which may be a result of dehydration from caffeine, alcohol, heat, and stress: all commonly found in people today.
Figure 4:
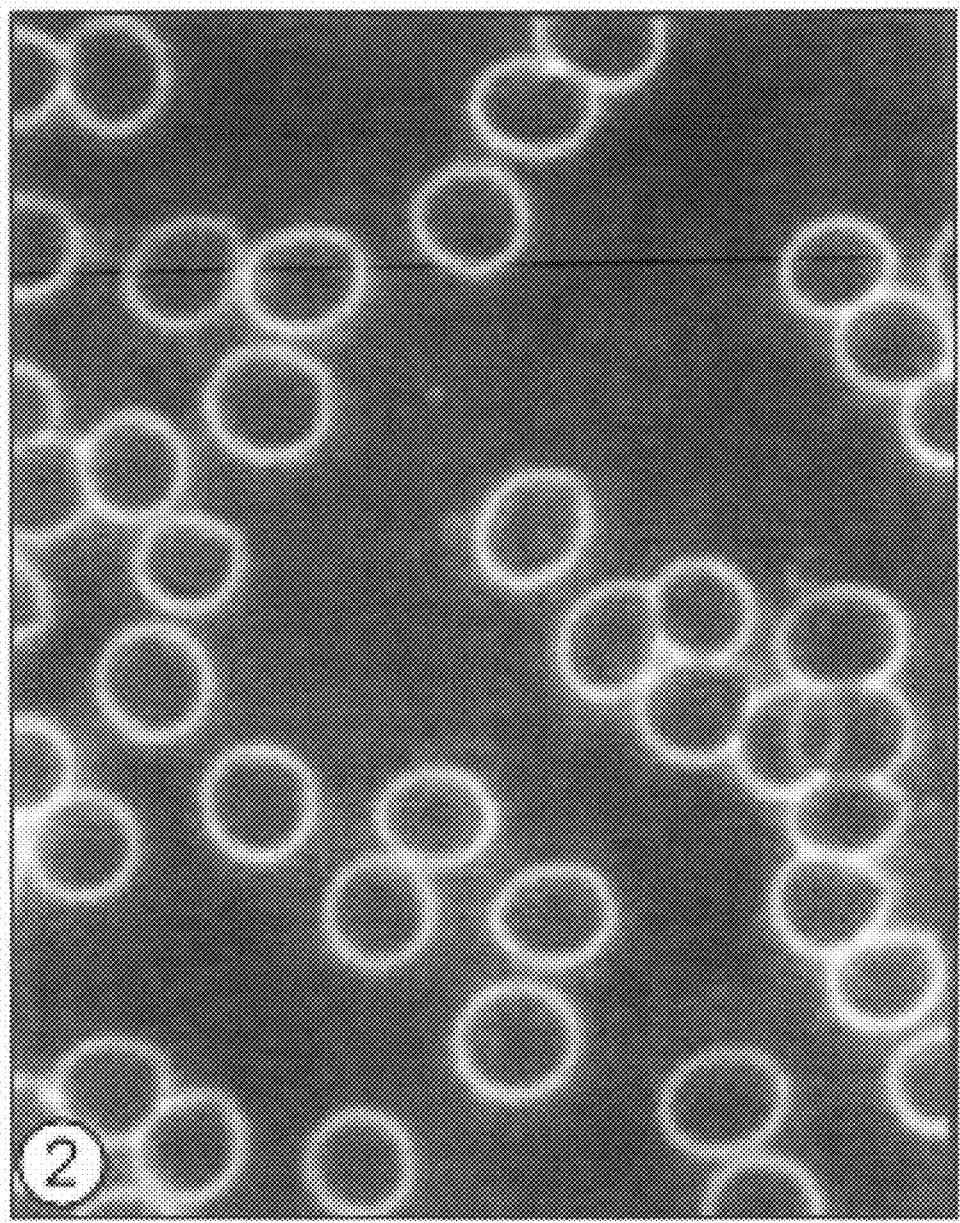
FIG. 4 shows blood cells which are treated by the mixture of 500 mg of Silica Hydride, a blend of Microcluster® silica (aggregates of 50 angstrom diameter micro sphere) and active hydrogen mixed with 8 oz of water for twenty minutes. The treated blood cells appear pristine, as if the substances trapped between the cells have been cleansed. The surface area of the cells has increased allowing exponentially more nutrients into the cells and more toxins to be removed.
Figure 5:
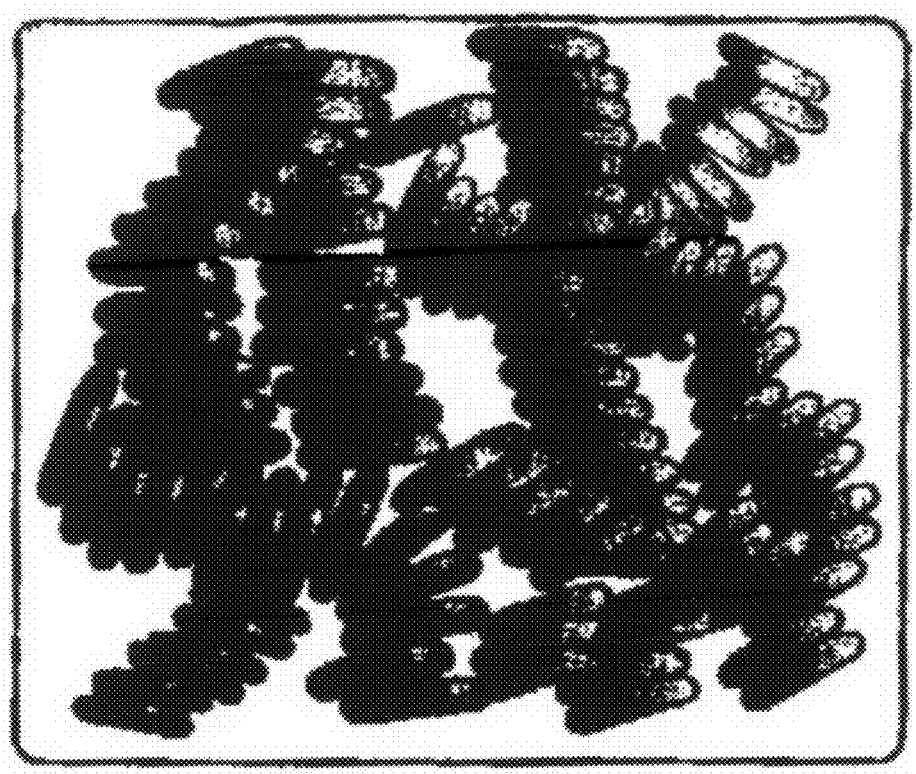
FIG. 5 shows a photomicrograph of the adult blood cell.
Figure 6:
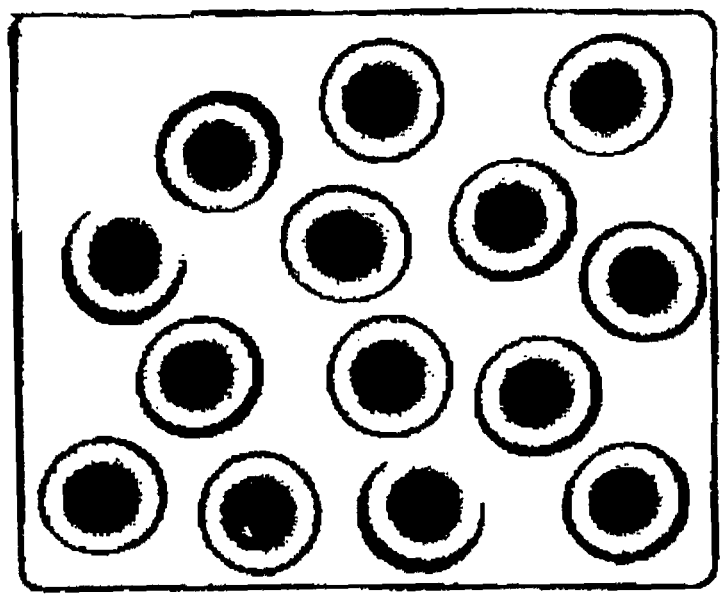
FIG. 6 shows a photomicrograph of the adult blood cell after eating or drinking

FIG. 2 is a schematic drawing of the procedure to make the digestible powder that generates hydride ion (H⁻) according to current application.

Various samples are prepared using the process shown as in the FIG. 1.

Samples of natural coral reef powder needs higher temperature and high vacuum to get a final product that generates hydrogen when dissolved in water. When the coral reefs are mixed with fine powders of magnesium, phosphorus, and potassium, the inventor can make the final product at a lower temperature and lower vacuum compared to the natural coral reef powder.

Example 1

The first step is to wash powder of natural coral reef (9), which was provided from market, with water (10).

The second step is to put the coral reef powder (9), washed with water, into the vacuum oven (2) and turn on the mechanical vacuum pump (7) at room temperature until the vacuum gauge reads $10^{-2}$ torr.

The third step is to increase the oven (2)'s temperature at a speed of 5° C./min up to 100° C. while the mechanical vacuum pump (7) is turned on. Then the vacuum pressure inside the vacuum oven (2) will increase due to coming out water.

The fourth step is to maintain the vacuum oven (2)'s temperature at 100° C. until the vacuum pressure reach down $10^{-2}$ torr. Remain at the temperature and vacuum pressure 30 minutes.

The fifth step is to increase the vacuum oven (2)'s temperature 5° C./min up to 600° C.

The diffusion pump (8) installed on the vacuum pump is turned on during the process. The sixth step is to maintain the oven (2) temperature at 600° C. and wait until the vacuum pressure reaches down to $10^{-5}$ torr.

The seventh step is to cool down the oven temperature down to 400° C. while the diffusion vacuum pump (8) is turned on.

The eighth step is to cut the vacuum line (11) that is located between the diffusion pump and open the hydrogen feed line (12) slowly. When the vacuum oven (2) pressure reaches 750 mm Hg, turn off the vacuum oven (2)'s heater (5) and vacuum pump (6).

The ninth step is to cool down the vacuum oven (2) to ambient temperature while making up the hydrogen to maintain the pressure at 760 mm Hg.

The tenth step is to close the hydrogen feed line (12) and open nitrogen feed line (13) and vent line (14). Blow nitrogen into the oven (2) at 770 mm Hg for 30 minutes.

The coral reef powders (9) treated as the previous ten steps emits hydrogen when dissolved in the water.

Example 2

The first step is to wash powder of natural coral reef (9), which is provided from market, with water (10).

The second step is to put the coral reef powder (9), washed with water, into the vacuum oven (2) and turn on the mechanical vacuum pump (7) at room temperature until the vacuum gauge reads $10^{-2}$ torr.

The third step is to mix the washed and dried coral reef powder (9) with mixture of magnesium, phosphorus, and potassium. Sources of the magnesium, phosphorous and potassium are, included but not limited to, $(NH_4)MgPO_4.6H_2O$ (struvite), $MgSO_4. KCl.H_2O$ (Kainite), $K_2SO_4.MgSO_4.6H_2O$ (Schönite), $K_2SO_4.MgSO_4.4H_2O$ (Leonite), and $K_2SO_4.2 MgSO_4$ (Langbeinite). Total content of the summation of the three elements are 1 grant per 100 gram of dried coral reefs. The weight ratio of magnesium:phosphorus:potassium is 2:4:4.

The fourth step is to increase the oven (2)'s temperature at a speed of 5° C./min up to 100° C. while the mechanical vacuum pump (7) is turned on. Then the vacuum pressure inside the vacuum oven (2) will increase due to coming out water.

The fifth step is to maintain the vacuum oven (2)'s temperature at 100° C. until the vacuum pressure reach down $10^{-2}$ torr. Remain at the temperature and vacuum pressure 30 minutes.

The sixth step is to increase the vacuum oven (2)'s temperature 5° C./min up to 600° C.

The seventh step is to maintain the oven (2) temperature at 600° C. and wait until the vacuum pressure reaches down to $10^{-2}$ torr.

The eighth step is to cool down the oven temperature down to 400° C. while the mechanical vacuum pump (7) is turned on.

The ninth step is to close the vacuum line (11) that is located between the mechanical vacuum pump (7) and open the hydrogen feed line (12) slowly. When the vacuum oven (2) pressure reaches 750 mm Hg, turn off the vacuum oven (2)'s heater (5) and vacuum pump (6).

The tenth step is to cool down the vacuum oven (2) to ambient temperature while making up the hydrogen to maintain the pressure at 760 mm Hg.

The eleventh step is to close the hydrogen feed line (12) and open nitrogen feed line (14) and vent line (15). Blow nitrogen into the oven (2) at 770 mm Hg for 30 minutes.

The coral reefs (9) treated as the previous eleven steps emits hydrogen when dissolved in the water.

Example 3

The first step is to wash powder of natural coral reef (9), which is provided from market, with water (10).

The second step is to put the washed coral reef powder (9) into the vacuum oven (2) and turn on the mechanical vacuum pump (7) at room temperature until the vacuum gauge reads $10^{-2}$ torr.

The third step is to mix the washed and dried coral reef powder (9) with mixture of magnesium, phosphorus, and potassium. Sources of the magnesium, phosphorous and potassium are, included but not limited to, $(NH_4)MgPO_4.6H_2O$ (struvite), $MgSO_4$. $KCl.H_2O$ (Kainite), $K_2SO_4.MgSO_4.6H_2O$ (Schönite), $K_2SO_4.MgSO_4.4H_2O$ (Leonite), and $K_2SO_4.2 MgSO_4$ (Langbeinite). Total content of the summation of the three elements are 2 gram per 100 gram of dried coral reefs. The weight ratio of magnesium:phosphorus:potassium is 1:1:1.

The fourth step is to increase the oven (2)'s temperature at a speed of 5° C./min up to 100° C. while the mechanical vacuum pump (7) is turned on. Then the vacuum pressure inside the vacuum oven (2) will increase due to coming out water.

The fifth step is to maintain the vacuum oven (2)'s temperature at 100° C. until the vacuum pressure reach down $10^{-2}$ torr Remain at the temperature and vacuum pressure 30 minutes.

The sixth step is to increase the vacuum oven (2)'s temperature 5° C./min up to 500° C. The seventh step is to maintain the oven (2) temperature at 500° C. and wait until the vacuum pressure reaches down to $10^{-2}$ torr.

The eighth step is to cool down the oven temperature down to 300° C. while the mechanical vacuum pump (7) is turned on.

The ninth step is to cut the vacuum line (11) that is located between the mechanical vacuum pump (7) and open the hydrogen feed line (12) slowly. When the vacuum oven (2) pressure reaches 750 mm Hg, turn off the vacuum oven (2)'s heater (5) and vacuum pump (6).

The tenth step is to cool down the vacuum oven (2) to ambient temperature while making up the hydrogen to maintain the pressure at 760 mm Hg.

The eleventh step is to close the hydrogen feed line (12) and open nitrogen feed line (14) and vent line (15). Blow nitrogen into the oven (2) at 770 mm Hg for 30 minutes.

The coral reefs (9) treated as the previous eleven steps emits hydrogen when dissolved in the water.

What is claimed is:

1. A method of manufacturing digestible powder that generates hydride ion (H) comprises of;
    the first step of washing natural coral reef powder with water, and
    the second step of putting the washed coral reef powder into a vacuum oven and turning on the mechanical vacuum pump at room temperature until the vacuum gauge reads $10^{-2}$ torr,
and
    the third step of to mixing the washed and dried coral reef powder with mixture of natural magnesium, phosphorus, and potassium source with a weight ratio of magnesium:phosphorus:potassium is 2:4:4 and with a total content of the summation of the magnesium, phosphorus, and potassium to be 1 gram per 100 gram of dried coral reef powder,
and
    the fourth step of increasing the oven's temperature at a speed of 5° C./min up to 100° C. while the mechanical vacuum pump is turned on,
and
    the fifth step of maintaining the vacuum oven's temperature at 100° C. until the vacuum pressure reach down $10^{-2}$ torr and remain at the temperature and vacuum pressure for 30 minutes,
and
    the sixth step of increase the vacuum oven's temperature 5° C./min up to 600° C.,
and
    the seventh step is to maintain the oven temperature at 600° C. and wait until the vacuum pressure reaches down to $10^{-2}$ torr,
and
    the eighth step of cooling down the oven temperature down to 400° C. while the mechanical vacuum pump is turned on,
and
    the ninth step of closing the vacuum line that is located between the mechanical vacuum pump and open the hydrogen feed line slowly until the vacuum oven pressure reaches 750 mm Hg and turning off the vacuum oven's heater and vacuum pump,
and
    the tenth step of cool down the vacuum oven to ambient temperature while making up the hydrogen to maintain the pressure at 760 mm Hg,
and
    the eleventh step of closing the hydrogen feed line and open nitrogen feed line and vent line followed by blowing nitrogen into the oven at 770 mm Hg for 30 minutes.

2. A method of manufacturing digestible powder that generates hydride ion (H⁻) of claim 1, wherein in the third step of to mixing the washed and dried coral reef powder with mixture of natural magnesium, phosphorus, and potassium source with a weight ratio of magnesium:phosphorus:potassium is 1:1:1 and with a total content of the summation of the magnesium, phosphorus, and potassium to be 2 gram per 100 gram of dried coral reef powder.

3. In the claims 1 or 2, the natural sources of the magnesium is $(NH_4)MgPO_4.6H_2O$ (Struvite).

4. In the claims 1 or 2, the natural sources of the magnesium is $MgSO_4.KCl.H_2O$ (Kainite).

5. In the claims 1 or 2, the natural sources of the magnesium is $K_2SO_4.MgSO_4.6H_2O$ (Schönite).

6. In the claims 1 or 2, the natural sources of the magnesium is $K_2SO_4.MgSO_4.4H_2O$ (Leonite).

7. In the claims 1 or 2, the natural sources of the magnesium is and $K_2SO_4.2 MgSO_4$ (Langbeinite).

8. In the claims 1 or 2, the natural sources of the phosphorous is $(NH_4)MgPO_4.6H_2O$ (struvite).

9. In the claims 1 or 2, the natural sources of the potassium is $MgSO_4.KCl.H_2O$ (Kainite).

10. In the claims 1 or 2, the natural sources of the potassium is $K_2SO_4. MgSO_4.6H_2O$ (Schönite).

11. In the claims 1 or 2, the natural sources of the potassium is $K_2SO_4.MgSO_4.4H_2O$ (Leonite).

12. In the claims 1 or 2, the natural sources of the potassium is $K_2SO_4.2MgSO_4$ (Langbeinite).

* * * * *